United States Patent
Schmidt et al.

(10) Patent No.: US 9,863,882 B2
(45) Date of Patent: Jan. 9, 2018

(54) VARIABLE THERMODYNAMIC RAMAN SPECTROSCOPY SYSTEM AND METHOD

(71) Applicant: The United States of America, as represented by the Secretary of Agriculture, Washington, DC (US)

(72) Inventors: Walter F. Schmidt, Glenn Dale, MD (US); Moon S. Kim, Silver Spring, MD (US); Kuanglin Chao, Ellicott City, MD (US); Daniel R. Shelton, Falls Church, VA (US); Catherine Leigh Broadhurst, Cloverly, MD (US)

(73) Assignee: The United States of America, as represented by The Secretary of Agriculture, Washington, DC (US)

( * ) Notice: Subject to any disclaimer, the term of this patent is extended or adjusted under 35 U.S.C. 154(b) by 48 days.

(21) Appl. No.: 15/012,372

(22) Filed: Feb. 1, 2016

(65) Prior Publication Data

US 2016/0223463 A1     Aug. 4, 2016

Related U.S. Application Data

(60) Provisional application No. 62/110,032, filed on Jan. 30, 2015.

(51) Int. Cl.
| | |
|---|---|
| *G01J 3/44* | (2006.01) |
| *G01N 21/65* | (2006.01) |
| *G01J 3/02* | (2006.01) |
| *G01N 1/44* | (2006.01) |
| *G01N 1/42* | (2006.01) |

(52) U.S. Cl.
CPC ............ *G01N 21/65* (2013.01); *G01J 3/0218* (2013.01); *G01J 3/0286* (2013.01); *G01J 3/44* (2013.01); *G01N 1/42* (2013.01); *G01N 1/44* (2013.01); *G01N 2201/08* (2013.01)

(58) Field of Classification Search
CPC ............... G01N 21/65; G01N 21/0303; G01N 2201/08; G01N 2201/0231; G01N 2201/06113; G01N 1/42; G01N 1/44; G01J 3/44; G01J 3/0218; G01J 3/0286; B01L 3/5085; H01L 23/40; H01L 23/3672

See application file for complete search history.

(56) References Cited

U.S. PATENT DOCUMENTS

| | | | | |
|---|---|---|---|---|
| 2003/0011997 | A1* | 1/2003 | Hsieh | ...................... H01L 23/40 361/708 |
| 2004/0233423 | A1* | 11/2004 | Nakayama | ......... G01N 21/0303 356/246 |
| 2014/0367702 | A1* | 12/2014 | Yamamoto | .......... H01L 23/3672 257/77 |
| 2016/0116334 | A1* | 4/2016 | Yang | ..................... B01L 3/5085 356/301 |

* cited by examiner

*Primary Examiner* — Jamil Ahmed
(74) *Attorney, Agent, or Firm* — John D. Fado; Robert D. Jones

(57) ABSTRACT

The variable thermodynamic Raman spectroscopy method and apparatus is a system for material analysis. In operation, a target material is subjected to a variable thermodynamic protocol and analyzed using a differential scanning calorimeter.

19 Claims, 12 Drawing Sheets

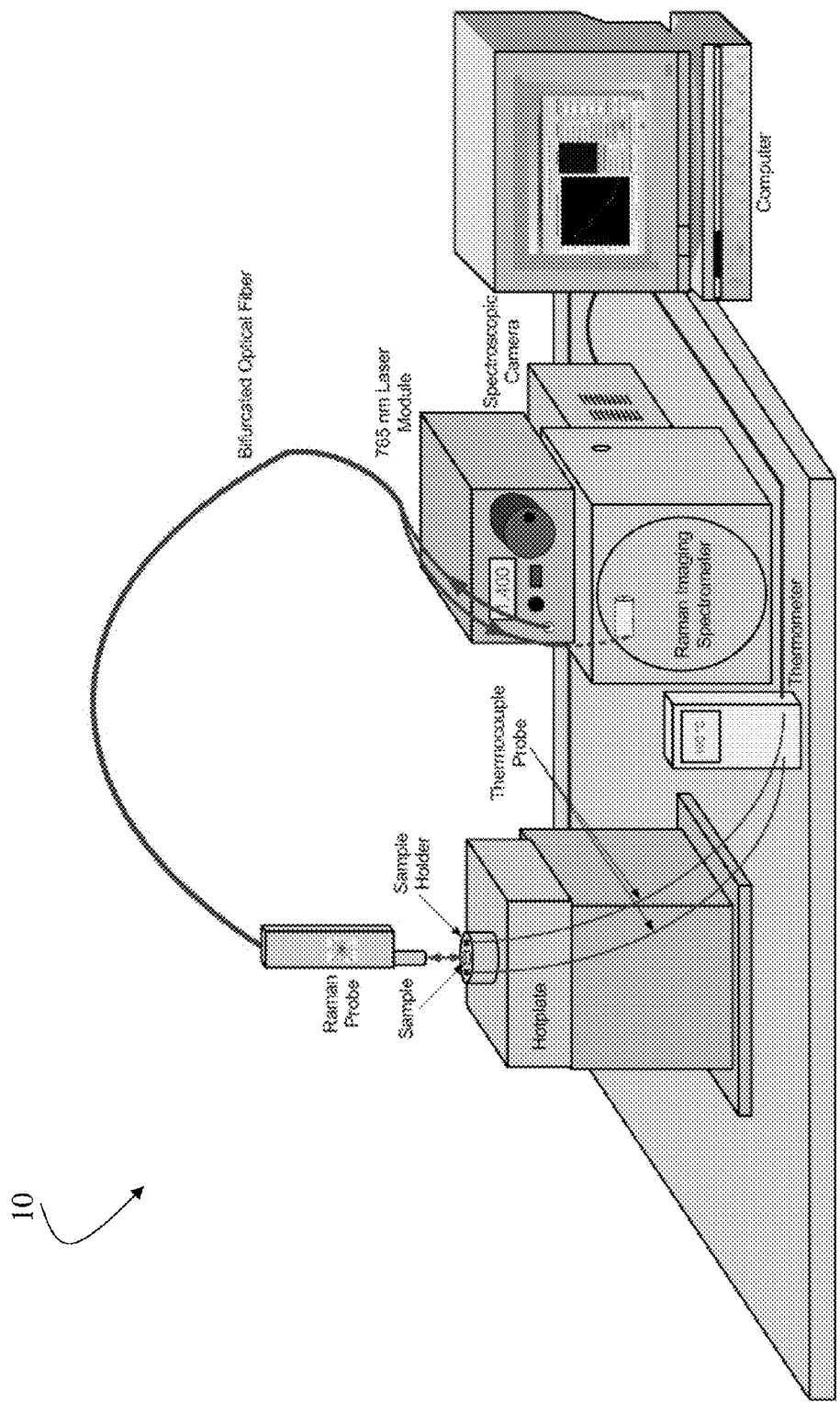
FIG. 1.A.

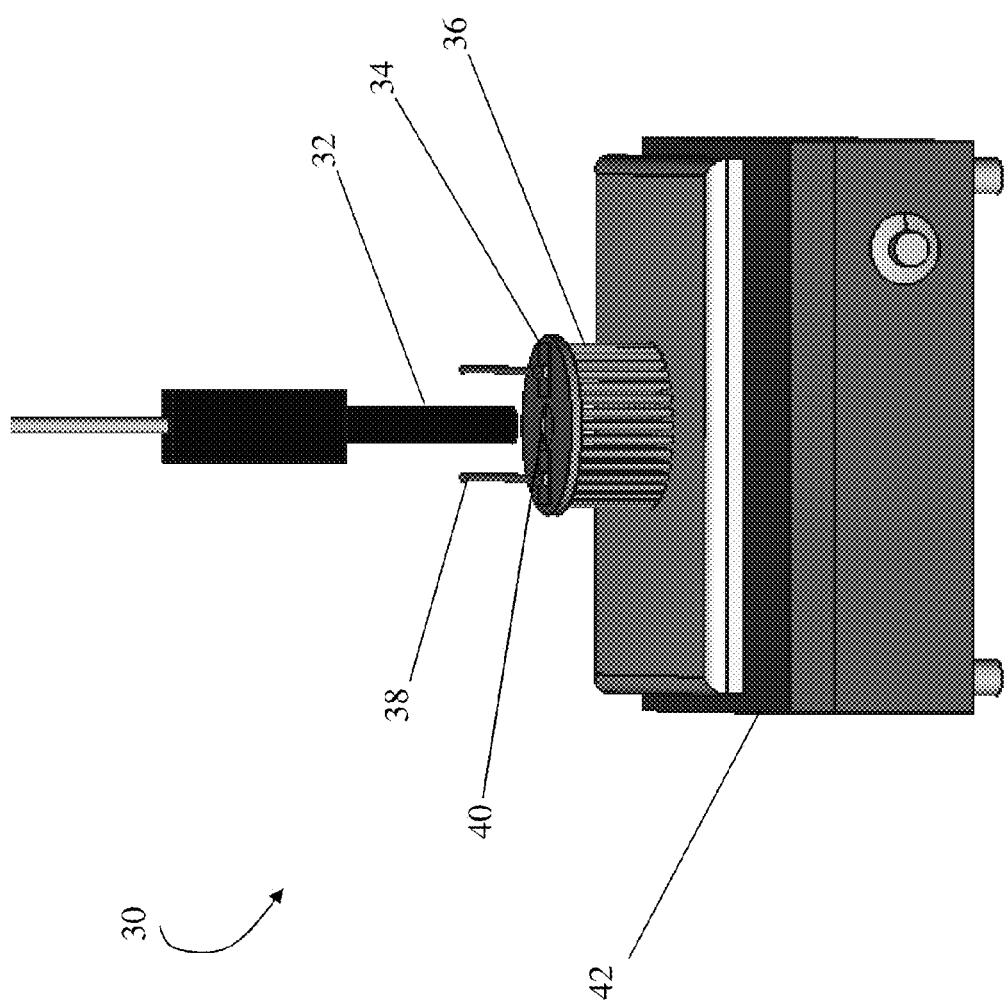
FIG. 1.B.

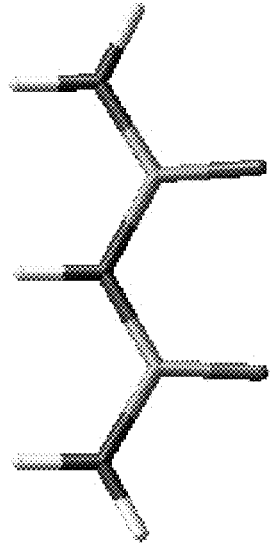
FIG. 2.A.
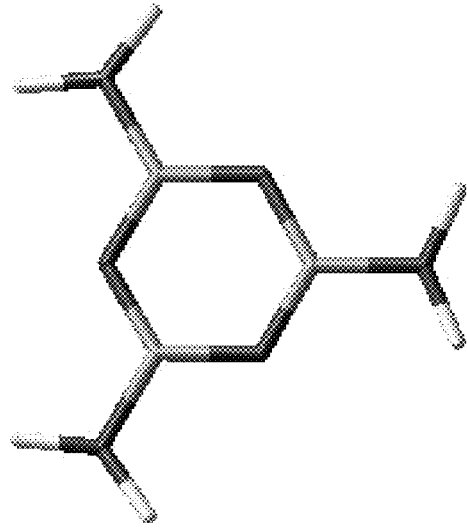
FIG. 2.B.
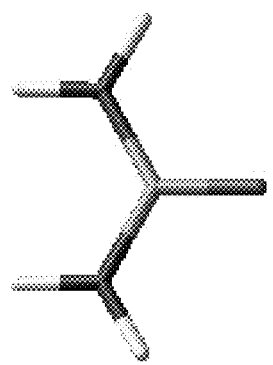
FIG. 2.C.
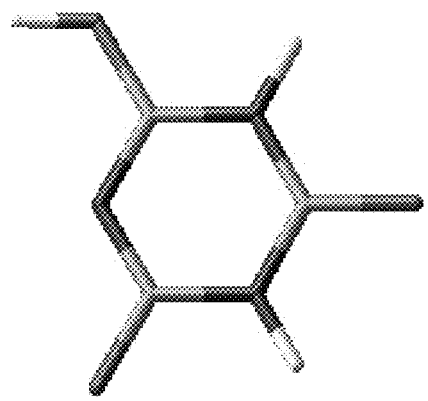
FIG. 2.D.

VARIABLE THERMODYNAMIC RAMAN SPECTROSCOPY SYSTEM AND METHOD

REFERENCE TO RELATED APPLICATIONS

This application claims the benefit of U.S. Provisional Application No. 62/110,032, filed Jan. 30, 2015, which is incorporated herein by reference in its entirety.

FIELD OF THE INVENTION

The disclosed method and apparatus relates to analyzing material samples and obtaining a unique signature/fingerprint using a new Raman spectral technique that identifies the most elastic sites within a material's molecular structure from the dynamic response to a temperature gradient. Specifically, the method and apparatus described herein relates to analyzing material (including adulterants) using Raman spectroscopy and enables concurrent collection of thermodynamic phase transition and spectral information in real-time as a function of temperature from approximately −200 to 400° C.

BACKGROUND OF THE INVENTION

Raman spectroscopy is an analytical technique used for rapid molecular-level fingerprinting of chemical substances, enabling (for example) real-time detection of contamination/adulteration of food, analysis of paints to determine art forgeries, and immediate identification of white powders that could be controlled substances. However, for any given molecular compound, the Raman spectral frequencies can be used to identify/confirm that compounds are actually fingerprints of specific structural fractions that make up the larger compound; structurally different molecular compounds can show similar fingerprints because they may have specific structural fractions in common. Raman spectroscopy relies on inelastic scattering, or Raman scattering, of monochromatic light, usually from a laser in the visible, near infrared, or near ultraviolet range.

The Raman effect occurs when electromagnetic radiation interacts with the polarizable electron density of a given Raman active molecule in the solid, liquid or gas phase. Typically, a sample is illuminated with a laser. Electromagnetic radiation from the illuminated spot is collected with a lens and sent through a monochromator. Elastic scattered radiation at the wavelength corresponding to the laser line (Rayleigh scattering) is filtered out. A small percentage of the laser light is inelastically scattered and interacts with the molecule, resulting in the energy of the laser photons being shifted up or down. This collected light is dispersed onto a detector by either a notch filter or a band pass filter. The shift in energy gives information about the vibrational modes in the system. Infrared spectroscopy yields similar, but complementary, information.

By design, Raman spectra are steady-state measurements. Heat causes more rigid sites within a molecule to increase in flexibility. When collecting Raman spectral measurements during an applied thermal gradient, some sites remain equally rigid during heating while other sites change flexibility in response to the temperature gradient. Variable temperature thermodynamic-based Raman spectroscopy (VTR) measurement techniques and apparatus described herein are unique because the temperature gradient enables distinguishing of vibrational modes that are due to kinetic processes from those that are due to steady-state processes; VTR identifies the precise temperature and/or temperature range over which molecular changes occur, and, concomitantly, the specific molecular sites most directly involved in these changes. The VTR method and apparatus described herein enables differentiation of more elastic sites (relatively temperature dependent vibrations) from more rigid sites (relatively temperature independent vibrations).

Although multiple spectroscopic techniques are available that detect molecular level changes in mobility, no instrumentation/methodology prior to the VTR process (described herein) reports and provides evidence for identifying molecular level sites of elasticity. The need exists for a Raman spectroscopic method and apparatus that can quickly and reliably distinguish similar compounds and provide molecular structural information for a target substance. The method and apparatus described herein provide a protocol and apparatus to enable a user to reliably identify compounds that are not readily distinguishable using conventional Raman spectroscopy as well as provide molecular structural information regarding a target substance.

SUMMARY OF THE INVENTION

This disclosure is directed to a variable thermodynamic Raman spectroscopy method and apparatus that is a system for material analysis. In operation, a target material is subjected to a variable thermodynamic protocol and analyzed using a differential scanning calorimeter.

This disclosure is also directed to a sample holder system. The system comprises a planar circular copper substrate. The substrate has multiple elongated prongs extending perpendicular to the substrate and vertically supports the substrate. A sample holder disposed in a center of the substrate so that the substrate holds a target sample. Thermocouples are positioned on a side of the substrate that is opposite from the prongs. A Raman probe is directed to the target sample on the substrate. The Raman probe acquires spectral data that is synced to the (corresponding) thermocouple data. A computer control system is in communication with the thermocouples and the Raman probe.

In operation, as the sample holder increases in temperature, the Raman probe acquires Raman spectral data for the sample, the data being synced with the corresponding thermocouple temperature data so that the spectral data is recorded with the corresponding temperature data. The data is analyzed to determine structural changes in the target sample molecules as the target sample changes temperature through the solid/liquid and liquid/gas phase changes.

BRIEF DESCRIPTION OF THE DRAWINGS

FIG. 1.A. Schematic view of the variable thermodynamic-based Raman (VTR) spectroscopic apparatus.

FIG. 1.B. Elevational view of the sample holder, Raman probe, and heating mechanism.

FIG. 1.C. Top view of the sample analysis system.

FIG. 1.D. Partial sectional view of an alternative embodiment of the analysis system along the section line D shown in FIG. 1.C.

FIG. 2.A. The amine structural analog for urea.

FIG. 2.B. The amine structural analog for biuret.

FIG. 2.C. The amine structural analog for cyanuric acid.

FIG. 2.D. The amine structural analog for melamine.

DETAILED DESCRIPTION OF PREFERRED EMBODIMENTS

Figure 3:
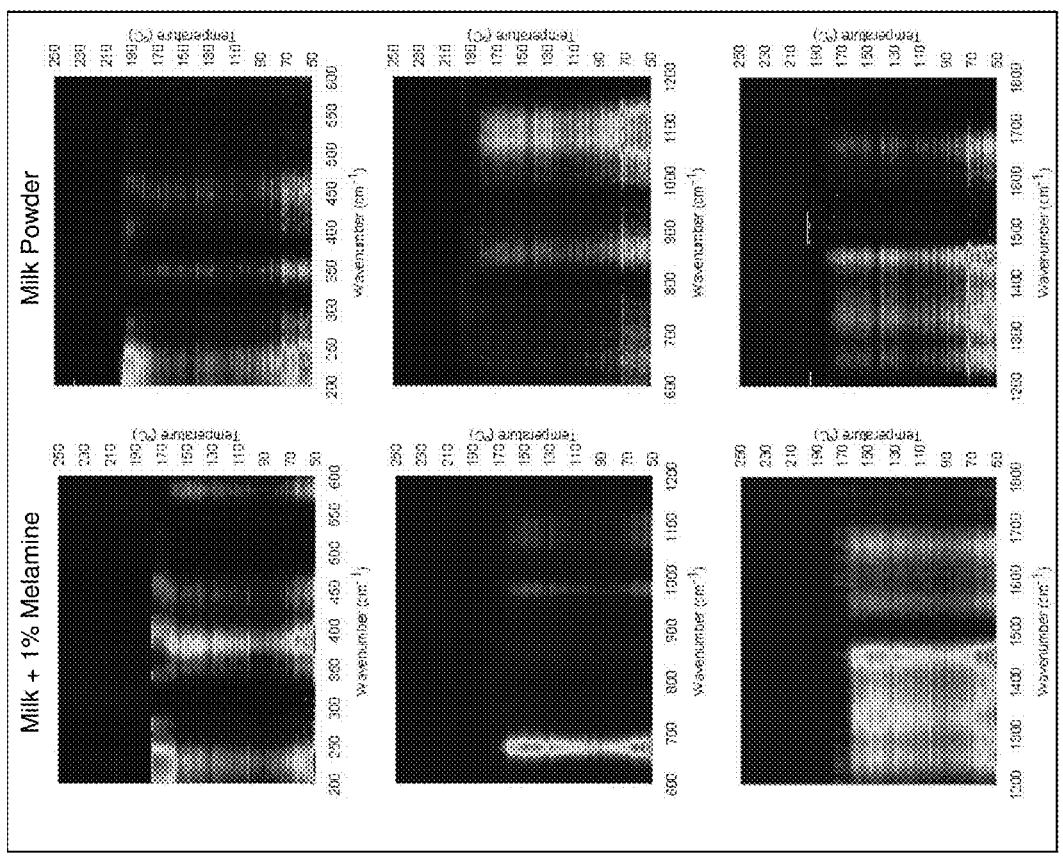
FIG. 3 The contour plot of intensity and frequency of selected major Raman spectral feature vs. temperature for 1% melamine in nonfat milk powder and control milk powder.

In accordance with the current method, extending Raman imaging spectroscopy from micro-scale or nano-scale point measurements and ambient temperatures to a technique capable of two-dimensional surface scans across wide temperature ranges provides a new avenue for the rapid acquisition of both practical and theoretical chemical data.

A practical application developed by the current inventors includes a hyperspectral Raman imaging system with sufficient spectral and spatial resolution to simultaneously identify and map (for example) four adulterant particles (ammonium sulfate, dicyandiamide, melamine, urea) mixed into dry milk at concentration levels from 0.1 to 5.0%. The hyperspectral imaging system maps a 25×25 $mm^2$ area in about 1 hr.

Rapid and accurate authentication of food ingredients is important for safety and quality evaluation. Raman chemical imaging coupled with appropriate mixture analysis algorithms can be used for simultaneous detection of multiple adulterants in many types of powdered food and nonfood materials. This system can also be used for macroscale imaging of food and agricultural products, such as scanning cross-sections of cut tomatoes for maturity evaluation. Significant wavenumber shifts in infrared and Raman spectra of solids with respect to temperature have been observed previously, and such data have the potential to readily identify contaminants, phase dissolution, and phase transitions.

For example, over the temperature range −30 to 22° C., previous researchers identified characteristic absorptions for both solid-state and liquid—solid-phase transitions in oleic acid with Fourier transform infrared spectroscopy. We have extended this study to Raman over the temperature range −150 to 60° C., greatly simplifying the spectral interpretation for this major edible lipid, which is abundant in olive and peanut oils and most nuts and meats.

The inventors further developed the technique of continuous variable thermodynamic-based Raman (VTR) spectroscopy to investigate isomerization of the organochlorine pesticide endosulfan between the nonsymmetric a- and symmetric b-diastereomers. Raman spectra were acquired at 1° C. intervals from 50 to 102° C. for a-endosulfan, b-endosulfan, and a 60/40 mixture.

For most vibrational modes discrete temperature-dependent changes occurred above 97° C. Dramatic changes occurred at 970, 1027, 1092, and 1350 $cm^{-1}$, where spectral density increased, peaks shifted, and peaks broadened substantially. The response of these modes indicated that the corresponding molecular sites are the most temperature-sensitive and therefore the most flexible. Results also preclude a to b-isomerization. A phase transition observed at 97-102° C. for b-endosulfan corresponded to the largest changes in the temperature-dependent Raman spectra.

Variable thermodynamic-based Raman provides a novel and very straightforward technique to identify theoretically proposed molecular rearrangements that occur just prior to phase transitions. In 2007, a widespread recall of pet foods occurred after thousands of dogs and cats in the United States experienced kidney failure. The United States Food and Drug Administration later determined that a Chinese-sourced wheat gluten ingredient was contaminated with melamine.

In 2008, some 300 Chinese children experienced kidney problems, including six fatalities, from melamine adulteration of infant formula produced by a major Chinese dairy company. In addition to melamine, adulteration of milk powder with fertilizers is facile and potentially introduces urea, biuret, triuret, and cyanamide to dairy products. Raman spectroscopy has been used previously to detect adulterants in dry milk including melamine, whey, ammonium sulfate, dicyandiamide, and urea.

Surface-enhanced Raman with Au or Au-coated colloidal microsphere greatly improves the detection limits for melamine in solution but has not been developed for dry mixtures. Hyperspectral imaging has the potential for inexpensive rapid throughput screening of multiple samples with minimal preparation and without solvents. If it is determined that any of the suspect contaminants occur in a particular sample, more precise, but also more expensive and time-consuming, analyses may be required.

Apparatus and Method

As generally shown in FIG. 1.A, the VTR apparatus 10 described herein comprises a Raman spectrometer (Raman Explorer 785, Headwall Photonics, Fitchburg, Mass.) fitted with a 16-bit charge-coupled device camera (1024 3 256 pixels; Newton DU920N-BR-DD, Andor Technology, South Windsor, Conn.). The spectrometer detects a Raman shift range of 102.2 to 2538.1 $cm^{-1}$ with a spectral resolution of 3.7 $cm^{-1}$. A 785 nm laser module (I0785MM0350MF-NL, Innovative Photonic Solutions, Monmouth Junction, N.J.) serves as the excitation source. A fiber optic Raman probe (RPB, InPhotonics, Norwood, Mass.) was used to focus the laser and acquire the Raman signals. A bifurcated fiber bundle delivers the laser radiation to the probe and transmits the Raman signals to the spectrometer. The Raman probe is in electronic communication with a computer comprising at least computer control, processing, recording, display, and other output functions.

More specifically, FIG. 1.B and FIG. 1.C shows the non-cryogenic/low temperature sample analysis system 30 of the apparatus 10 in greater detail. Specifically, FIG. 1.B. shows the Raman probe 32, copper heat sink 34, heat sink interface 36, thermocouple 38, an aluminum sample holder 40, and heater/hot plate 42. FIG. 1.C shows a top view schematic of the heat sink 34 in greater detail. FIG. 1.D.

shows an alternative embodiment of the sample analysis system 30 wherein the system 30 is modified to conduct cryogenic analysis.

With regard to the non-cryogenic/low temperature system shown in FIGS. 1.B. and 1.C., in operation, a target sample is placed in the sample holder 40 in the copper heat sink 34 and heated by the hot plate 42. As the sample is heated, the Raman probe 32 directs a laser to the sample and acquires Raman spectral data as the temperature of the sample changes. The heat sink interface ("prongs") 36 enable a more gradual and controlled heating of the sample. The circular shape of the of the heat sink 34 also ensures that the sample holder 40 is equidistant from the periphery of the heat sink 34 (and attached prongs 36) so that a target sample is heated evenly regardless of the structure of the heating device (i.e. the hot plate 42). The thermocouples 38 monitor the temperature of the copper heat sink 34 and sample holder 40, and provide temperature data to a control system which syncs the temperature data with the changing Raman spectra.

With regard to the cryogenic/low temperature system shown 50 in FIG. 1.D., the system 50 is used to investigate the solid states of materials that are liquid or gas at ambient temperatures. To accomplish this analysis, an aluminum sample cup 60 is placed in a flange cut into the sample holder copper heat sink 54. The heat sink 54 is either pre-chilled or placed in a cryogen bath (liquid nitrogen or dry ice/acetone) and the temperature increases as the cryogen evaporates. Testing and calibration provides the combination of cryogen volume and heat appropriate for the desired rate of temperature increase for a given sample.

The inventors utilized the cryogenic modification to investigate the solid state and solid-to-liquid state transitions in polyunsaturated fatty acids including linoleic, docosahexanoic and docosapentaenoic acid. These molecules have melting temperatures as low at $-78°$ C. and solid state phase transitions in the range $-100$ to $-10°$ C. The inventors have discovered very dynamic molecular behavior prior to melting which is spectroscopically undetectable without utilizing the VTR system.

The process of using the cryogenic/low temperature 50 is similar to the system of using the non-cryogenic/low temperature system 30. As primarily shown in FIG. 1.D., in operation, a target sample is placed in the aluminum sample holder 60 in the copper heat sink 54. A heating device may (or may not) be used to heat the system 50. As the sample warms, the Raman probe 32 (of the type shown in FIGS. 1.A. and 1.B.) directs a laser to the sample and acquires Raman spectra as the temperature of the sample changes. The thermocouples 58 monitor the temperature of the copper heat sink 54 and sample holder 60, and provide temperature data to a control system which syncs (i.e. pairs) the temperature data with the corresponding Raman spectral data, as the temperature of the sample changes.

Example Study One

In this example, hyperspectral Raman was used for rapid screening of solid-phase samples for potential adulterants. Mixture analysis algorithms were improved by defining a temperature range in which the contaminant spectrum changes dramatically and uniquely compared with unadulterated material. Raman spectra were acquired for urea, biuret, cyanuric acid, and melamine (pure and at 1% in dried milk powder) from 50 to 310° C. with a gradient of 1° C. $\text{min}^{-1}$. Adulterants were clearly identified in the milk powder.

Specific frequencies that were mainly associated with ring breathing, stretching, and in-plane deformation shifted with respect to temperature up to 12 $\text{cm}^{-1}$ in all four molecules. Specific frequencies significantly increased/decreased in intensity within narrow temperature ranges independent of whether the amine was mixed in milk. Correlation of Raman and differential scanning calorimetry data identified structural components and vibrational modes, which concur with or trigger phase transitions.

Skim dry milk was purchased from a local supermarket. The four reagents (melamine, urea, cyanuric acid, and biuret) were mixed into the milk powder at 1.0% in 50 ml polypropylene centrifuge tubes. A vortex mixer was used to ensure uniform distribution of the adulterant particles. Powder samples were placed in copper sample holders 40 and heated on a ceramic hotplate 42. Copper heat sinks 34 were placed between the ceramic heat surface 42 and the sample holder 40 to slow the rate of temperature increase.

Two K-type thermocouple probes 38 were attached to two sides of the sample area and connected to a dual-input thermometer (EasyView EA15, Extech Instruments, Nashua, N.H.). The sample temperature was defined as the average value of the two probes 38. The Raman probe 32, hotplate 42, and sample materials were placed in a closed black box to avoid ambient light. The hot plate heater was set for a gradient of about 1° C. $\text{min}^{-1}$.

Raman spectra were acquired from 50 to 250° C. for urea and biuret and 50 to 310° C. for cyanuric acid and melamine. If dramatic chemical-thermal rearrangement occurred at a temperature prior to 250° C., that temperature was the maximum used. The inventors did not use a set time schedule for spectral acquisition, but rather acquired spectra each time the sample temperature increased 1° C. System software was developed using LabVIEW (National Instruments, Austin, Tex.) to fulfill functions such as camera control, data acquisition, temperature measurement, and synchronization.

Differential Scanning calorimetry (DSC)

One milligram of each amine was placed in an aluminum sample pan with a crimped lid. An empty pan was used as control. Samples were placed in a DSC Q200 differential scanning calorimeter (TA Instruments, New Castle, Del.) and scanned from 50° C. to approximately 20° C. above the melting point (mp). A thermocouple under each pan recorded the rate of heat absorbed versus the rate applied. Heating rate was 5 or 10° C. $\text{min}^{-1}$ depending on the melting temperature. Samples were protected from oxidation using a continuous supply of $N_2$, which is heated at the same rate as the sample, then pumped into the heating chamber.

Results

Figure 4:
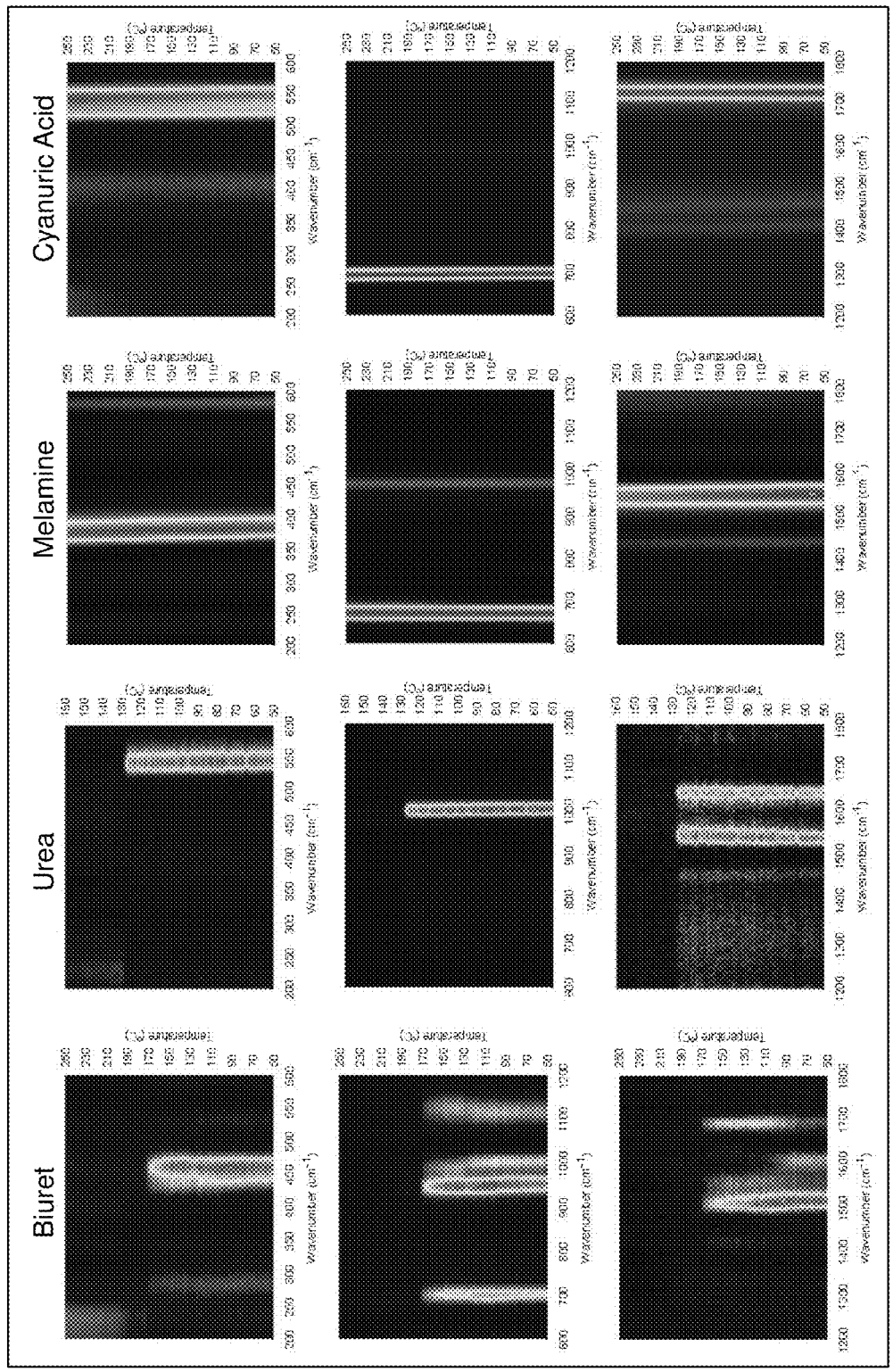
FIG. 4 Overview of contour plots of intensity and frequency of selected major Raman spectral features vs. temperature for urea, biuret, cyanuric acid, and melamine.
Figure 5:
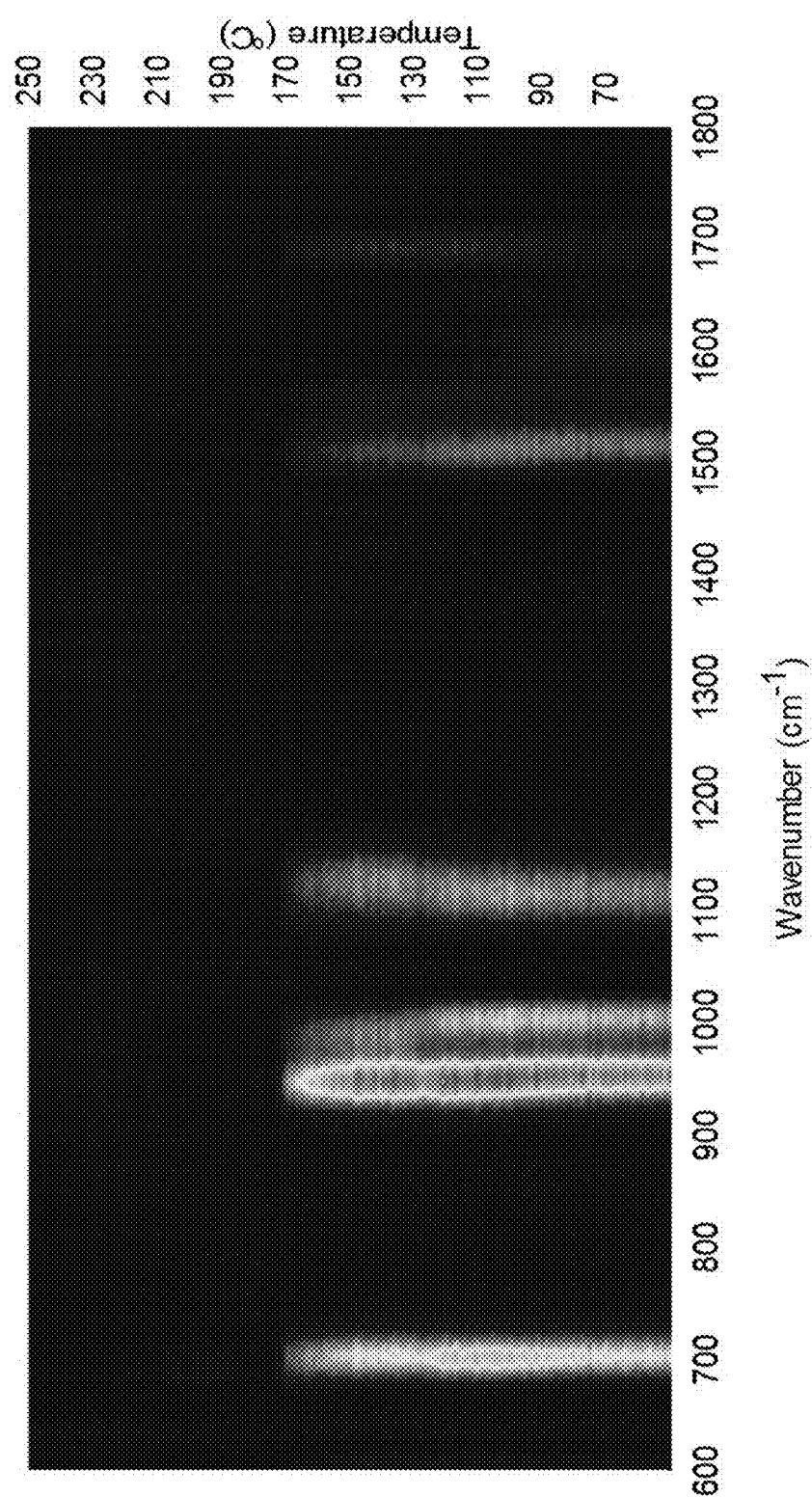
FIG. 5 Detail of significant frequency shifts vs. temperature from FIG. 4.
Figure 6:
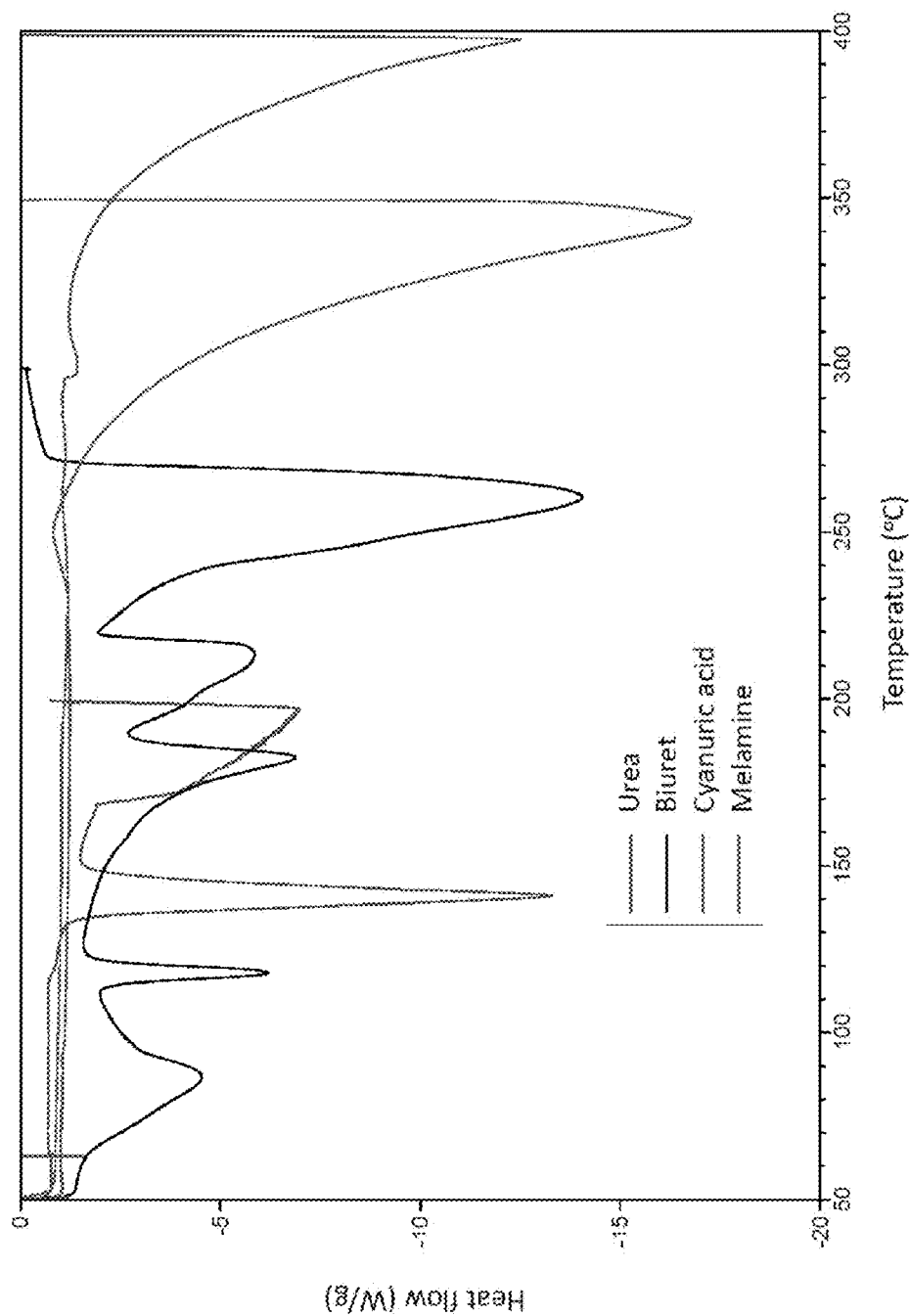
FIG. 6 Differential scanning calorimetry heat absorption curves for urea, biuret, cyanuric acid, and melamine. Note multiple absorptions in biuret prior to and after melting (193° C.).

As shown in Urea, FIGS. 2A-D., biuret, cyanuric acid, and melamine contain overlapping structural components; however, each structural analog has markedly different physical properties (e.g., m.p. urea 133; biuret 193; cyanuric acid, 330; melamine, 345° C.). FIG. 3 shows that 1% melamine in milk powder is clearly detectable, as are the other three amines. FIGS. 4 and 5 are contour plots showing the progressive Raman frequency shifts with increasing temperature. Shifts are significant with respect to line bandwidth and are specific to individual molecules and individual molecular sites; spectra are truncated at melting. FIG. 6 shows DSC data for three of the molecules over the temperature range of the current experiments.

Assignments of chemical structure to temperature-dependent Raman vibrational modes agree with previously reported Raman frequencies observed at a constant temperature (Table I).

Urea

The major temperature-dependent Raman vibrational modes in urea ($CH_4N_2O$) at 50° C. are 548, 1006, 1543, and 1649 $cm^{-1}$. All shift in frequency with temperature; the three largest shifts are a decrease at 544 $cm^{-1}$ (in-plane deformation), and increases at 1543 and at 1645 $cm^{-1}$ (amide III N—H stretching and $NH_2$ asymmetric bending). Urea is symmetrical about the O=C axis and at all four H sites; the flexibility of N—H groups is equal. Gradually, both 1543 cm-1 (N—H asymmetrical stretching) and 1649 cm-1 ($NH_2$ asymmetrical bending) increase in frequency.

A structural explanation for the temperature-dependent Raman data is that one of the four N—H sites become longer than (i.e., unequal to) the other three, and therefore asymmetrical vibrational modes increase in intensity. In FIG. 6 these shifts correspond to the shoulder of the sharp peak of increasing heat flow indicating the melting of urea.

Biuret.

The temperature-dependent Raman and DSC data for biuret are very different from urea, even though chemically biuret is the dimer of urea. The major vibrational modes at 50° C. are 281, 456, 703, 954, 1007, 1116, 1517, and 1605 $cm^{-1}$. Despite their similar structure, only one frequency is within 5 cm-1 of those in urea (1005 cm-1). A second peak in biuret shows up at 1550 cm-1 only above about 130° C., whereas the [O=C—N—H]NH asymmetric bending frequency in urea occurs only below 130° C.

DSC peaks (FIG. 6) indicate two solid-state phase transitions (at ~70 and 130° C.) prior to the peak for melting at 193° C. This correlates with FIG. 4 and Table I (see footnotes), where some observed frequencies decrease sharply when 70° C. and then 130° C. are reached, yet others increase after 130° C. The center of the biuret molecule is an N—H group between two O=C sites. Because each site is an amide (O=C—N—H), the two sites can be coplanar, and the NH will always be either above or below this plane. The increase in frequency at 456 $cm^{-1}$ and change in intensity at 954 $cm^{-1}$ (C—N—C bending) is consistent with a change in twist between the two O=C sites.

Biuret has a discrete temperature profile: at 90° C. the 1605 $cm^{-1}$ peak intensity decreases dramatically (O=C—N—H symmetrical NH bending) at 110° C., 1005 $cm^{-1}$ peak intensity (N—C—N stretching) is at its maximum; concurrently at 130° C., peaks at 462 $cm^{-1}$ and 990 $cm^{-1}$ appear (C—O inplane bending and symmetrical skeletal stretching, respectively). The simplest structural interpretation is that at 50° C., the two amide groups are not coplanar, but at 110° C., they are. The intensity of the 1698 $cm^{-1}$ peak increases above 80° C. and is maximized at 130° C. Since this peak is assignable to a planar b-turn in an amide, this also indicates biuret is planar at that temperature. The changes near 990 $cm^{-1}$ and at 1120 $cm^{-1}$ would then correspond to changes in flexibility of $NH_2$, NH, or both moieties above and below the plane.

Cyanuric Acid

The three most intense VTR frequencies in cyanuric acid at 110° C. are 547, 700, and 1729 $cm^{-1}$. Four other significant frequencies (FIG. 5) are also observed (411, 987, 1416, and 1470 $cm^{-1}$). Structurally, cyanuric acid is a cyclic trimer of urea, and the peak a 547 $cm^{-1}$ assignable to in plane deformation is similar to 549 $cm^{-1}$ in urea. The peak at 411 $cm^{-1}$ is assignable to ring deformation. The narrowing of temperature-dependent Raman peaks with minimal or no frequency shift at 1727 $cm^{-1}$ (O=C stretching) and at 700 $cm^{-1}$ (ring N—H site flexibility) indicates these sites in the ring (O=C—NH—(O=C)—NH) become more rigid with increasing temperature, and since the peak at 987 $cm^{-1}$ decreases, the applied thermal stress also reduces symmetrical ring stretching.

The VTR frequency shift in cyanuric acid at 539 $cm^{-1}$ (in-plane deformation) is non-uniform, narrowing to 240° C. and then broadening to 290° C. Concurrent with the broadening is an increase in intensity at 403 $cm^{-1}$ (ring deformation) and an additional peak at 458 $cm^{-1}$ (C—O in-plane bending). Thus at about 270° C., the N=C—N site in the ring is deformed, and C—O bending at this C site becomes planar. The N—C=N bond sequence becomes a less planar—asymmetrical component of the ring resonance structure above 250° C. One explanation for the asymmetry and frequency shift in the temperature-dependent Raman peak at 547 $cm^{-1}$ from 110° C. is that at the lower temperature, one of two O=C—NH is more flexible than the other. The increasing concurrence in the coplanar conformation of the two O=C—NH sites with temperature explains the very high thermal stability of cyanuric acid.

Spectra are observed over 290° C. in FIG. 4. The DSC curve (FIG. 6) indicates the onset of melting at 330° C. as reported; however, the thermal absorption curve is broad with a shallow slope and extends nearly 70 degrees, in concurrence with a 12 $cm^{-1}$ shift in the ring stretching frequency, which is the largest shift the inventors observed overall.

Melamine

Melamine is a structural analog of cyanuric acid in which —$NH_2$ sites replace —OH sites or N=C—$N_2$ sites replaces O=C—$N_2$. Five major temperature-dependent Raman frequencies are observed at 50° C.: 385, 582, 672, 980, and 1557 $cm^{-1}$. The only temperature-dependent Raman vibrational mode similar between melamine and cyanuric acid is a relatively weak symmetrical skeletal stretching frequency (981 $cm^{-1}$ in melamine, 987 $cm^{-1}$ in cyanuric acid). Melamine, urea, and biuret all have vibrational modes of NH and $NH_2$ sites in common near 1557 $cm^{-1}$.

Structurally, melamine has no N—H ring sites, but three N=C—N—$H_2$ sites are present per molecule. The spectral lines at 582 $cm^{-1}$ and 980 $cm^{-1}$ are ring breathing and symmetrical skeletal stretching, respectively. Their signal intensities are very weak compared with 385 $cm^{-1}$ (C—N bending out of plane), 672 $cm^{-1}$ (NH2 in-plane bending) and 1557 $cm^{-1}$ (NH symmetrical stretching).

Melamine has the highest reported melting temperature of the four amines but may decompose near melting, which agrees with FIG. 4. The sites that absorb thermal energy are C—N and C—N—H sites external to ring structure. The 385 cm-1 frequency can be one of three sites; if the N in C—N—H is bending out of plane, NH sites also will be out of plane. With increasing temperature, the peak at 1557 $cm^{-1}$ shifts to 1551 $cm^{-1}$ and also the peak sharpens. In-plane $NH_2$ bending (672 $cm^{-1}$) shifts upfield 2 $cm^{-1}$, and ring breathing at 582 $cm^{-1}$ steadily decreases. An explanation consistent with these results is that with increasing temperature, the ring structure overall becomes more rigid, and two of the $NH_2$ sites become more planar, but one C—N site bends more out of plane. This molecular site becomes progressively more unequal, i.e., above or below the stable ring plane. The increase with temperature in out-of-plane bending may disrupt the uniformity of packing between melamine molecules, resulting in the broad melt/decomposition peak in the DSC data starting at about 250° C. and continuing to 345° C. (FIG. 6).

Mechanism for Variable Thermodynamic-Based Raman Selectivity

Melting and other thermally induced phase transitions correspond at the molecular level to an increase in flexibility in response to thermal stress. Near their individual melting points, molecules become more flexible. Specific sites within a molecule may become flexible before the entire molecule responds. Under thermal stress, more rigid molecules or sites respond less quickly than more flexible sites. The pattern in which vibrational modes respond to thermal stress is unique to a specific molecular structure. Physical phase transitions in polymers, biopolymers, and oleic acid spectroscopy correlated with temperature have been reported using infrared or Raman spectroscopy. However in these studies measurements were made at discrete, discontinuous temperature steps under steady state conditions.

The inventors' spectra was collected with a continuous temperature gradient, which minimizes the time (and molecular pathways) in which thermal relaxation between individual temperature measurement steps can occur. A temperature gradient consistently perturbs steady state conditions, resulting in thermal stress. Molecular sites more sensitive to thermal stress will absorb thermal energy at lower temperatures than less sensitive sites.

For example, although the stereoisomers and b-endosulfan contain identical structural components, each has discrete marker vibrational modes. In the b-isomer, the seven-membered ring is symmetrical, whereas the ring is asymmetrical in the a-isomer. The flexibility of the asymmetrical seven-membered ring accounts for its physical properties: the a-isomer melts at 108° C. and environmentally concentrates in air. The rigidity of the symmetrical conformation in the b-isomer accounts for its melting point of 208° C. and the fact that it is found as an environmental contaminant in water, not air.

Figure 7:
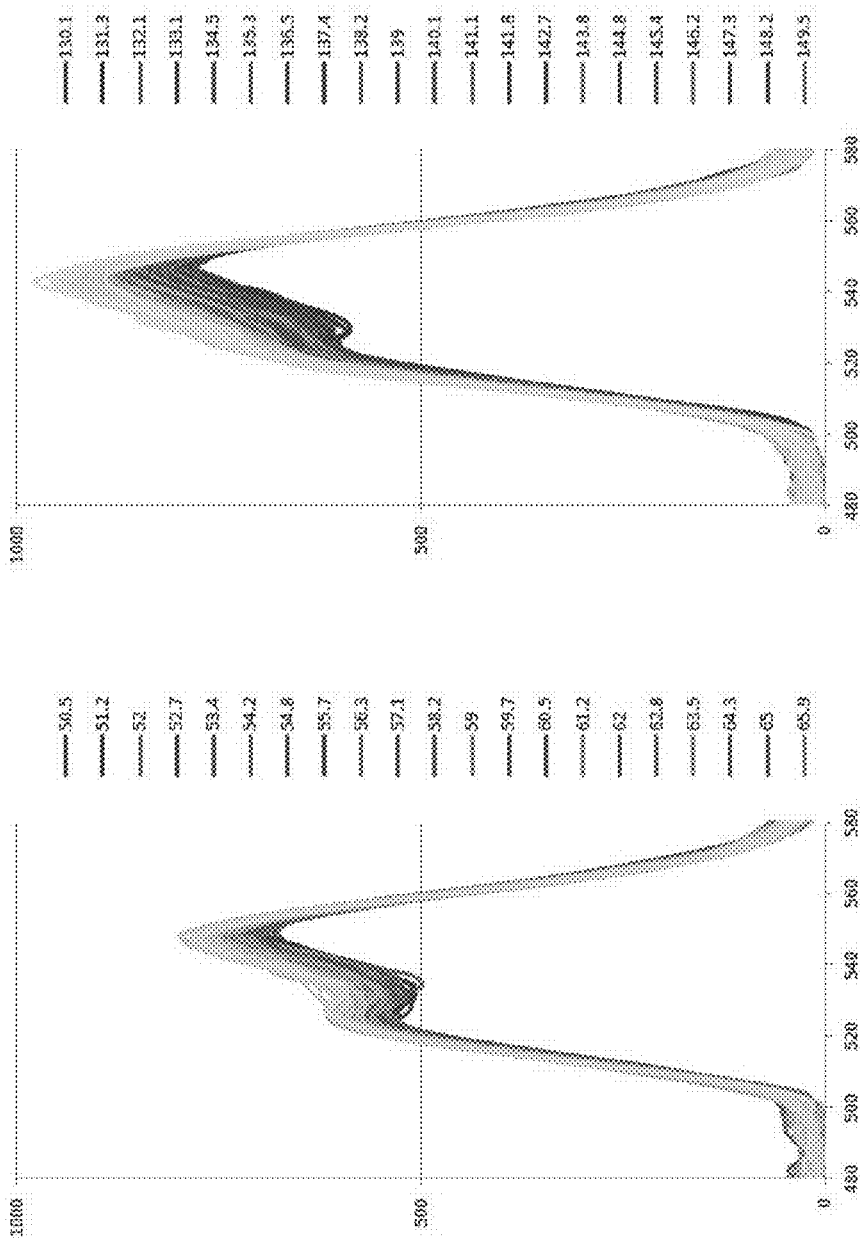
FIG. 7 Normalized relative intensity of the cyanuric acid 537 $cm^{-1}$ in-plane deformation peak vs. temperature, showing increased intensity 130° C.
Figure 8:
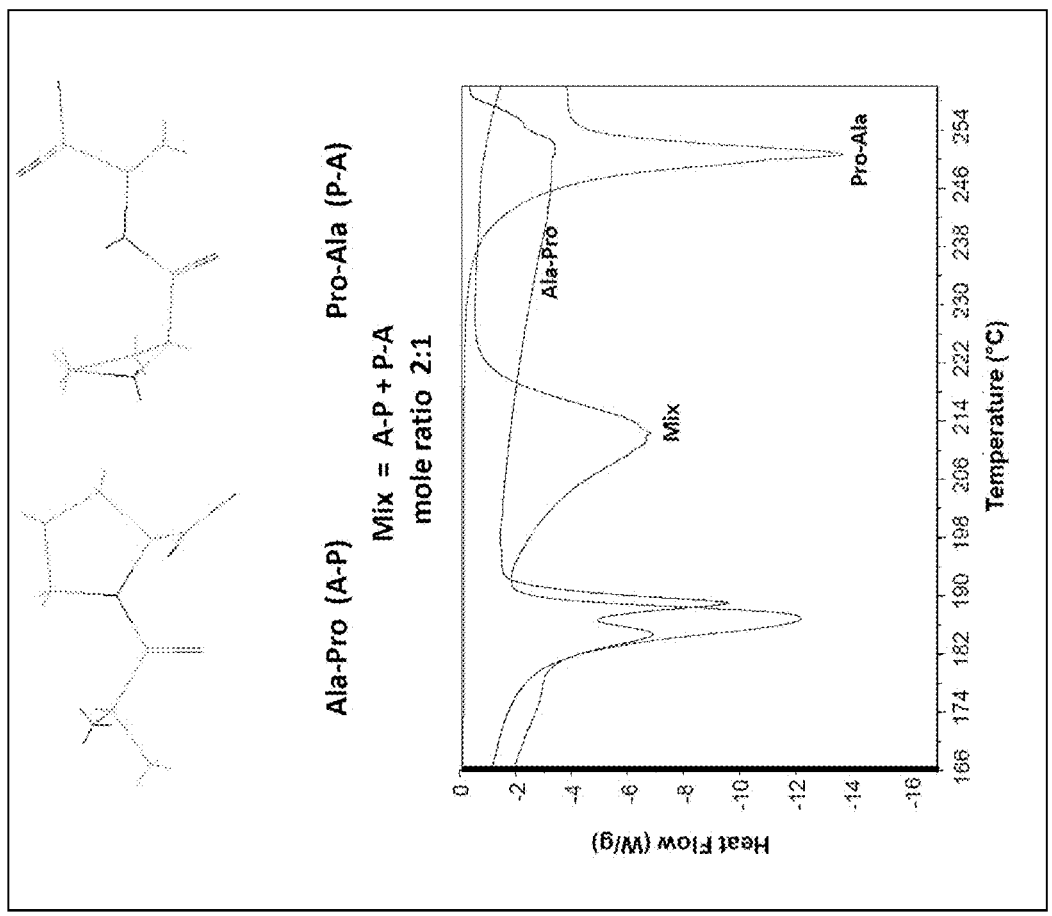
FIG. 8 Differential scanning calorimetry heat absorption data for Ala-Pro, Pro-Ala and a 2/1 mixture.
Figure 9:
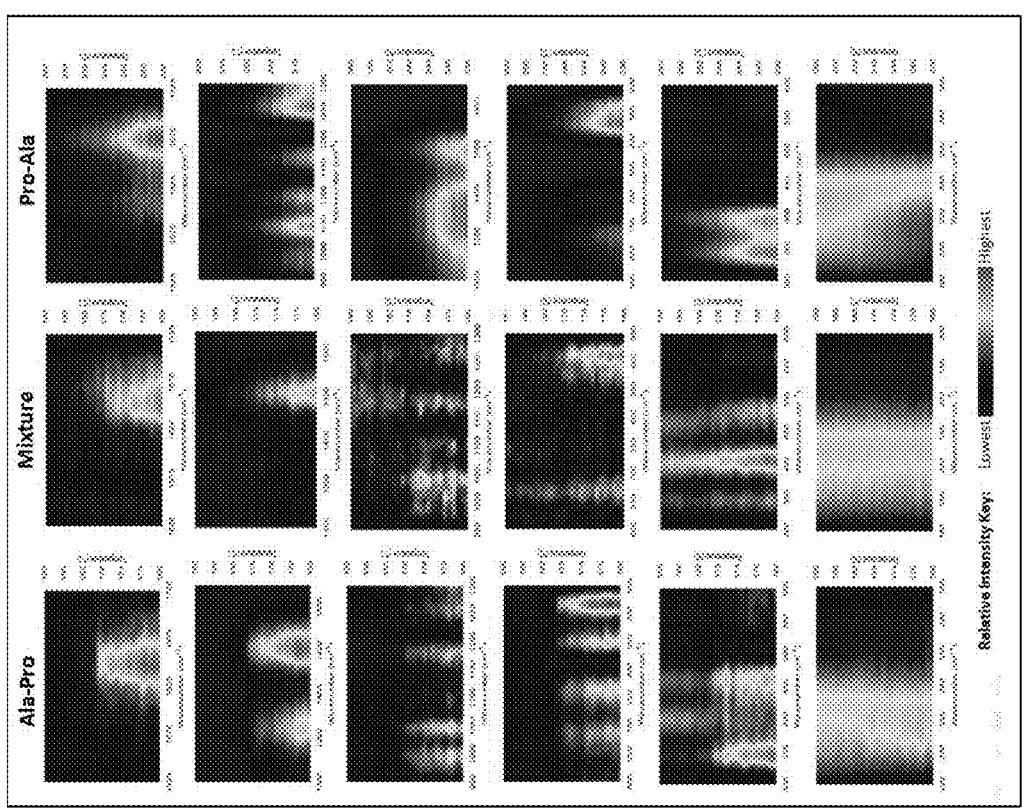
FIG. 9 Temperature dependent Raman contour spectra for Ala-Pro (a), Pro-Ala (c) and Ala-Pro/Pro-Ala 2:1 (b). Peak intensity is scaled from blue (lowest) to red (highest). TDR signal intensity was normalized at each temperature prior to generating contour plots, and the temperature range utilized corresponds to the sharp phase transition area observed in FIG. 8.
Figure 10:
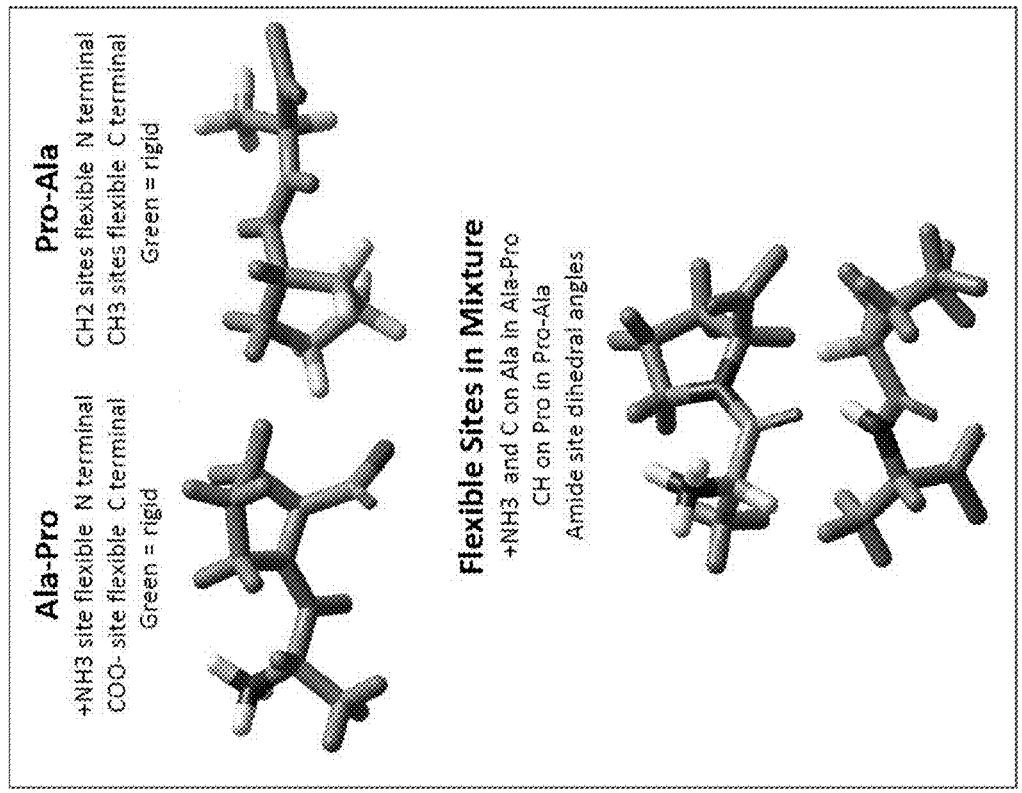
FIG. 10 Flexible and rigid (all green) sites at temperatures approaching phase transitions in Ala-Pro, Pro-Ala, and Pro/Pro-Ala 2:1.
Figure 11:
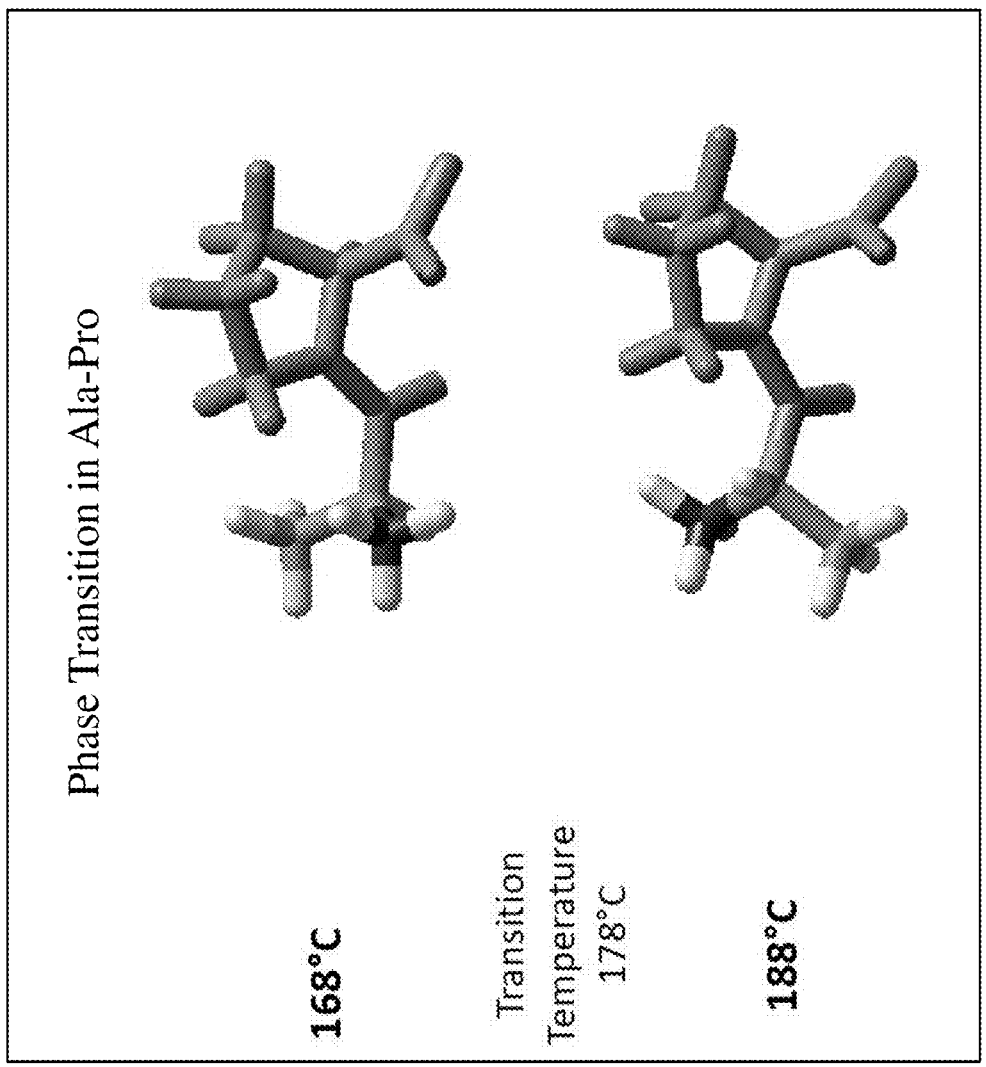
FIG. 11 Conformation shift in Ala-Pro at 178° C. phase transition.

In FIG. 7 the intensity of the cyanuric acid 537 $cm^{-1}$ inplane deformation peak is nearly doubled at temperatures over 130° C. Similar magnitude changes in peak intensity were described for biuret above. Although temperature-dependent Raman spectra of melamine can be observed to 310° C., 1% melamine in milk is not detected above 170° C. At ~120° C. milk proteins and sugars will begin to react irreversibly, forming Maillard or "browning" products. Upon heating, significant peaks in 1% melamine in milk occur in the 1200-1400 $cm^{-1}$ range, which are not observed for either of the component structures.

The inventors assert that the methods described herein could confirm if these are sites where melamine and milk protein chemically react. Thus VTR can enable detection of melamine even if it chemically reacts with a food product during processing. These are just a few of many examples of VTR frequencies that increase, decrease, appear, or disappear within specific temperature ranges that often correlate with known phase transitions and may correlate with chemical reactions. Hyperspectral analysis can be improved because the current inventors described a straightforward method to rule out structural analogs that can cause considerable uncertainty, time, and effort with other analytical methods.

Recently, vibrational spectroscopy in the THz range has been used to identify melamine in several food products. A fingerprint spectrum can be assignable to a portion of a chemical structure or to some physical form of a chemical structure. Structural elucidation is a fundamental and critical component in spectroscopic techniques to avoid both false positive and false negative analytical results.

VTR spectroscopy may also be useful for identifying environmental triazine contamination in soils and composts. Soils are more complex substrates than milk powder; however, response to increasing temperature for organic soil constituents will undoubtedly differ from that of clay minerals, potentially enhancing detection of individual organic species. Fractions bound tightly to soils may also be identified more easily than with other methods. Temperature-dependent Raman spectra are not identical to constant temperature Raman spectra because VTR spectra are transient. In constant temperature experiments any unequal absorption of thermal energy absorbed selectively site-to-site within a molecular structure will relax and redistribute evenly. In the inventors' temperature-dependent Raman experiments, the temperature gradient is continuous; therefore assigned frequencies that are unaffected by temperature can be distinguished from vibrational modes that alter with temperature, especially within the temperature range in which phase transitions occur. Within this gradient, any thermal sequence in which individual molecular sites become more or less flexible can be determined. This information is an identifying component unique to that individual molecular structure.

Since VTR enables the temperature-dependent components of Raman spectra to be identified, these vibrational modes can be assigned to chemical structures. This in turn enables identification of individual vibrational modes and chemical structure components that concur with or trigger the start of a phase transition.

Example Study Two

Variable thermodynamic-based Raman (VTR) spectroscopy applies the temperature gradients utilized in differential scanning calorimetry (DSC) to Raman spectroscopy, providing a straightforward technique to identify molecular rearrangements that occur just prior to phase transitions. Herein the inventors apply VTR and DSC to the dipeptides Ala-Pro, Pro-Ala, and the mixture Ala-Pro/Pro-Ala 2:1. A simple change in residue order resulted in dramatic changes in thermal stability and properties. Characteristic Pro vibrations were observed at ~75° C. higher temperature in Pro-Ala than Ala-Pro. The appearance/disappearance of characteristic vibrational modes with increasing temperature showed that a double peak in the Ala-Pro major phase transition (174-184° C.) was due to a 165 degree rotation of $H_3C$—$C^*$—$NH_3$ about $C^*$. $CH_3$ asym. bending and $CH_2$ rocking and wagging frequencies present in Pro-Ala were not observed in Ala-Pro. For Ala-Pro, the Ala $NH_3$, and Pro $COO^-$ sites were flexible whereas the Pro ring moiety was not; since the O═C—N (—C)$_2$ amide bond is planar the C—N—C moiety keeps the Pro ring rigid. For Pro-Ala, $CH_2$ sites in the Pro ring were flexible; the O═C—NH amide bond is perpendicular to the Pro ring thus $^+NH_3$ frequencies 650-850 $cm^{-1}$ were not observed. Since the mass of the Pro ring is significantly larger than the mass of the flexible Ala $^+NH_3$ moiety, Pro-Ala absorbs more thermal energy, corresponding to a higher phase transition temperature (240-260° C.). Ala-Pro, Pro-Ala, and Ala-Pro/Pro-Ala 2:1 exhibited α-helix, β-sheet, α-helix secondary structure conformations, respectively.

Introduction

Although flexibility in peptide and protein structures is critically important, identifying flexibility at multiple sites simultaneously is elusive. In particular, structural changes involved in the thermal adaptation of proteins are considered manifold and complex. Every day, billions of people consume animal or plant proteins subjected to high degrees of thermal stress (i.e. cooking, canning, processing); yet quantifying the processes involved in the thermal transformation of proteins remains as much a culinary art as a science. Most current analytical techniques applied cover only a very limited portion of the motion occurring in protein structures.

A correlation between thermostability and rigidity of protein structures is well documented. The corresponding state hypothesis argues that proteins show a similar structural flexibility at their adapted temperature. At room temperature, thermophilic proteins exhibit reduced flexibility and appear more rigid compared to mesophilic or psychrophilic proteins. However thermophilic proteins become more flexible at the relatively higher temperatures at which they function.

Proline is an atypical amino acid with the N atom part of a five membered ring, thus it contains a $^+NH_2$ zwitterion site instead of $^+NH_3$, and the phi ($\varphi$) angular range in peptide bond formation is highly restricted. Proline can readily adopt cis- and trans-configurations. The cis-configuration accounts allows prolyls to bend the regional amino acid alignment and therefore fold the protein. Proline rich tandem-repeat domains are an important factor in protein flexibility. However Polypro linker peptides (all trans-) are highly rigid and linear.

On average thermophilic/hyperthermophilic proteins have relatively higher concentrations of Pro that mesophilic/psychrophilic proteins, with Pro tending to be at the N-terminal of an $\alpha$-helix. Proteins are universally stabilized by Pro residues at the N-terminal of an $\alpha$-helix, regardless of their overall thermostability. Exposed and flexible sites are more conducive to the Pro effect.

Raman spectroscopy has been utilized to characterize primary and secondary structure in small unfolded peptides and proteins. Raman has significant advantages over IR spectroscopy in this capacity because it is insensitive to water absorption. Vibrational modes from crystalline, solid (hydrated or not), amorphous aggregate and aqueous phases can be characterized with equal precision. Our research group has developed the technique of variable thermodynamic-based Raman spectroscopy (VTR), which applies the precise temperature gradients utilized in differential scanning calorimetry (DSC) to Raman spectroscopy. DSC is powerful technique to quantify the heat absorption of amino acids, peptides and proteins, providing information regarding phase transitions and fundamental thermodynamic properties, but not on the mechanisms by which heat is absorbed at the molecular level. However, the VTR technique identifies specific temperature ranges where flexible structures absorb heat and the molecular-level response to that thermal stress. VTR provides a very rapid and straightforward technique to identify theoretically proposed molecular rearrangements that occur just prior to phase transitions.

For example, Raman spectra of the organochlorine pesticide endosulfan were acquired at 1° C. intervals from 50-102° C. for $\alpha$-endosulfan, $\beta$-endosulfan and a 60/40 mixture. A phase transition observed at 97-102° C. for $\beta$-endosulfan corresponded to the largest shifts in the VTR spectra. The shifts identified a molecular pathway for the transition because discrete sets of molecular sites progressively increased in flexibility with increasing temperature. An irreversible pathway for the isomerization from the symmetrical $\beta$-isomer to the nonsymmetric $\alpha$-isomers was confirmed.

Similarly, Raman spectra were acquired for urea, biuret, cyanuric acid and melamine (pure and at 1% in dried milk powder) from 50-310° C. Vibrational modes that were mainly associated with ring breathing, stretching and in-plane deformation shifted with respect to temperature in all four molecules[26]. Specific frequencies significantly increased/decreased in intensity within narrow temperature ranges independent of whether the amine was mixed in milk. Correlation of Raman and DSC data identified vibrational modes and the molecular sites assigned to them which are temperature sensitive, especially just prior to phase transitions. Results suggest flexible molecular sites in solid structures absorb thermal energy before more rigid sites do. Herein the inventors apply the VTR technique to the dipeptide structural analogs, Ala-Pro and Pro-Ala, and correlate the results with DSC.

Materials and Methods

The VTR system utilizes a Raman spectrometer (Raman Explorer 785, Headwall Photonics, Fitchburg, Mass.) fitted with a 16-bit CCD camera (1024×256 pixels; Newton DU920N-BR-DD, Andor Technology, South Windsor, Conn.). The spectrometer detects a Raman shift range of 102.2 to 2538.1 cm$^{-1}$ with a spectral resolution of 3.7 cm$^{-1}$. A 785-nm laser module (I0785MM0350MF-NL, Innovative Photonic Solutions, Monmouth Junction, N.J.) served as the excitation source. A fiber optic Raman probe (RPB, InPhotonics, Norwood, Mass.) was used to focus the laser and acquire the Raman signals. A bifurcated fiber bundle delivers the laser radiation to the probe and transmits the Raman signals to the spectrometer. Laboratory-grade reagents (Sigma-Aldrich, >98%) were utilized. The mixture Ala-Pro/Pro-Ala 2:1 was also investigated to minimize ambiguity in spectral assignments. Ten milligram samples were placed in copper holders and analyzed.

For DSC data 1.0 mg of each peptide was scanned in a crimp-sealed aluminum sample pan. the inventors utilized a Q200 differential scanning calorimeter (TA Instruments, New Castle, Del.); heating rate 10° C. min$^{-1}$ from 50° C. to 300° C. (~20° C. above the melting point of the pure amino acids) under continuous $N_2$ heated at the same rate as the sample. All samples for both instruments were run in triplicate and each dataset analyzed independently to ensure reproducibility.

Results and Discussion

The DSC results showed very different heat absorption functions for the two dipeptides (FIG. 1). Ala-Pro exhibited a phase transition starting at about 170° C. whereas Pro-Ala did not exhibit a phase transition until 240° C. The phase transition temperature range for both was ~24° C., so there was no overlap. Ala-Pro had a relatively sharp phase transition 174-184° C. with two distinct regions centered on 180° C. A broader transition followed at 206-256° C. Pro-Ala had a single sharp phase transition temperature region between 240-260° C. DSC data for the cooling path as well as re-running samples showed that this phase transition is reversible. The DSC data for Ala-Pro/Pro-Ala 2:1 yields a curve that is intermediate between the two end members, indicating that Pro-Ala and Ala-Pro interacted as they were heated.

Vibrational modes are given in Table 1, and were assigned from the component Ala and Pro residues. A few VTR spectral features were identical in both structures, e.g. 209 cm$^{-1}$ (COO$^-$ twisting), 348 cm$^{-1}$ (amide C—C—N twisting) and 1351 cm$^{-1}$ (CH$_3$ asym bending). The major VTR frequencies discrete to Pro-Ala were 238 cm$^{-1}$ and 882 cm$^{-1}$ (Pro ring bending and ring stretching) and 1381 cm$^{-1}$ (Ala CH$_3$ asymmetric bending). The major VTR frequencies discrete to Ala-Pro were 756 cm$^{-1}$ (Pro COO$^-$ wagging); 848 cm$^{-1}$, 914 cm$^{-1}$, 996 cm$^{-1}$, and 1047 cm$^{-1}$ ($^+$NH$_3$ twisting and rocking).

FIG. 2 shows spectral contour plots for the 24° C. temperature range that includes the phase transitions observed with DSC. Signal intensity was normalized at each temperature prior to generating the plots. In these plots VTR spectra of Ala-Pro and Pro-Ala differ markedly. $CH_3$ asym. bending and $CH_2$ rocking and wagging frequencies present in Pro-Ala are not observed in Ala-Pro. Specific vibrational modes in Pro-Ala are observed at a higher temperature than in Ala-Pro. A slower response to thermal stress and/or response at a relatively higher temperature correlates with greater rigidity, and agrees with the DSC data.

In VTR, the absence of peaks corresponds to rigidity. Since the $^+NH_2$ torsion and $COO^-$ wagging frequencies are not present in Pro-Ala at 240° C., these sites do not increase in flexibility with increasing temperature; when these sites are rigid, others must become more flexible. In contrast, in Ala-Pro, both the $^+NH_3$ and the $COO^-$ vibrational modes are observed at higher temperature, suggesting that both ends of the dipeptide remain flexible, but there is a virtual absence of vibrational modes assignable to the Pro ring structure (FIG. 3).

In previous publications, Mukhopadhyay et al. assigned amide vibrational modes (ca. 300-500 $cm^{-1}$) from φ and ψ angles for Ala-dipeptides in aqueous solution. In their terminology, Pro-Ala has $α_r$ and Ala-Pro has PPII structure. The inventors observed very similar frequencies in the solid state: in Pro-Ala, peaks near 340 and 395 $cm^{-1}$ are both positive; in Ala-Pro, peaks near 352 $cm^{-1}$ are positive but peaks near 400 $cm^{-1}$ sum to near zero (Table 1). The dihedral angle difference between PPII (φ=−68° and ψ=135°) and $α_r$ (φ=−73° and ψ=−30°) is about 170° [i.e. $φ_1−φ_2=−68°−(−73°)=5°$; $ψ_1−ψ_2=135°−(−30°)=165°$]. This difference equals a 10° flexibility from 180° at one end of the amide (5° at each end). Assuming the C═O end of the amide is the more rigid, this could explain the flexibility observed in the $CH_2$ ring vibrational modes in Pro-Ala. Flexibility at both ends would explain the Ala-Pro VTR spectra.

A structural analog of the planar amide group O═C—N—H (mass 43) has the last backbone atoms in the opposite direction [down versus up the backbone sequence]: O═C—C*H (mass 41). Each proton results in a torsional force above, below, or in the amide plane relative to the amide bond. Ala-Pro has no O═C—N—H structure so the only torsional amide component arises from the O═C—C*H structure. Due to its lower mass, the O═C—C*H Raman vibrational frequencies are proportionally lower than the corresponding O═C—N—H frequencies. Torsional vibrational modes for $^+NH_3$ include structural components from the dihedral angle H—N—C*—H. Above 178° C., increased $^+NH_3$ rocking motion is consistent with disrupting this N—H and C*—H dihedral angle linked to the oriented conformation below 178° C. (FIG. 4). The only VTR frequencies which appear above 180° C. (395 and 440 $cm^{-1}$) are from the new orientation, i.e. a rotation of 165 degrees from the former conformation. This change corresponds with the 174-184° C. reversible phase transition (FIG. 1) in which two distinct DSC regions centered on 180° C. are observed for the single peptide.

A previous VTR study of biuret showed a very strong vibrational mode near 400 $cm^{-1}$ but no vibrations peaks in the 325-364 $cm^{-1}$ range and a phase transition at 170° C. Biuret ($H_2N(C$═$O)$—$NH$—$(C$═$O)$—$NH_2$) contains four repeating O═C—N—H groups and no amide O═C—C*H structures. The 170° C. phase transition and the sites involved could be structurally related to the 178° C. phase transition in Ala-Pro.

In Pro-Ala the H in O═C—C*H can be above or below the amide plane. A consequence of $CH_2$ and C*H proline ring flexibility is that the C* proton will be equally likely above and below the amide plane, i.e. the average torsional angle for O═C—C*H will be near zero. Under increased thermal stress, the average torsional angle H—C*—N—H between Pro and Ala will remain close to 0 or 180 degrees. The orientation in which $^+NH_2$ and $COO^-$ groups are on the same half of the molecule has lower energy than when they are on opposite halves. However, broad VTR peaks for $CH_3$ bending centered near 1374 $cm^{-1}$ indicates both symmetrical and asymmetrical methyl bending frequencies are equally present. This suggests that about half the time, H—N—C*—H torsional angles are cis-(0°), the other half the time, this torsional angle will be trans-(180°). Because the two forms have very similar thermal properties, only a single DSC peak is observed, and increasing thermal stress would have limited effect on any specific conformation(s).

Pro-Ala with only one planar amide group has phase transition at 245° C. Cyanuric acid and melamine also contain precisely planar sites (O═C—N—H and N═C—N—H, respectively). Phase transitions ~290° C. in cyanuric acid and melamine correspond to N—H amide out-of-plane bending. The N—H group transition from in-plane to out-of-plane is a vibrational mode common all three molecules observed in the definitive VTR peaks in the 300-500 $cm^{-1}$ region.

For Ala-Pro/Pro-Ala (2:1), the temperature range is identical to that of Ala-Pro, but $CH_3$ symmetrical and asymmetrical bending frequencies (1320-1420 $cm^{-1}$), $^+NH_3$ torsion (850 $cm^{-1}$), and $COO^-$ wagging (762 $cm^{-1}$) are not apparent. The three sites most flexible in the mixture are: CH rocking (1265 and 1038 $cm^{-1}$), $^+NH_3$ rocking and torsion (1076 and 483 $cm^{-1}$), and amide group bending torsion (1651 $cm^{-1}$ and 402 $cm^{-1}$). The $^+NH_3$ peak at 483 $cm^{-1}$ shifts to 474 $cm^{-1}$, (δ=−14 $cm^{-1}$) and narrows, whereas the peak starting at 1176 $cm^{-1}$ shifts 1181 $cm^{-1}$, (δ=5 $cm^{-1}$) and broadens. In the mixture, as temperature increases the same site that is flexible in Ala-Pro switches vibrational energy from a $^+NH_3$ torsional mode to a $^+NH_3$ rocking mode. For Pro-Ala in the mixture, a significant decrease in CH rocking releases torsional energy at the amide which occurs concurrent with the loss of the β-sheet amide frequency and appearance of an α-helical frequency (FIG. 3). In contrast, in Pro-Ala alone the amide bond vibrational modes arise from the symmetrical β-sheet orientation.

CONCLUSION

VTR spectra can precisely identify multiple flexible molecular structures in pure peptides or in mixtures, even when the sites are on structurally distinct molecules. At temperatures lower than a phase transition or "melting point," insufficient thermal energy is available for all the vibrational modes to be fully occupied. In a temperature gradient, more flexible sites will absorb thermal energy earlier than more rigid sites. Overall structural elucidation requires explaining the modes which cease to be observed as well as those which are observed and/or newly observed as temperature increased. The simplest explanation for the loss in intensity at a specific temperature is that additional thermal energy cannot be absorbed with those specific vibrational modes. As a practical methodology, the ability to identify flexible sites requires a temperature gradient in which the heating rate is comparable to the relaxation rate of the signal. If the gradient is too weak, the transient signal component of the Raman spectra may be too slow to be observed. Latent heat can relax surprisingly slowly.

The results document the pivotal effect that Pro can have on peptide flexibility and molecular order. For both dipeptides, the amino acid with the free $^+$NH site was routinely more flexible. Flexible sites absorb thermal energy faster and have more available vibrational modes. For Ala-Pro, the Ala $^+$NH$_3$, and Pro COO$^-$ sites were flexible whereas the Pro ring moiety was not; since the O=C—N(—C)$_2$ amide bond is planar (FIG. 3), the C—N—C moiety keeps the Pro ring planar, i.e. rigid.

In contrast, for Pro-Ala, CH$_2$ sites in the Pro ring were flexible; since the O=C—NH amide bond is perpendicular to the Pro ring, there is no steric hindrance to ring flexibility and the $^+$NH$_3$ frequencies in the range 650 to 850 cm$^{-1}$ were not observed. Since the mass of the flexible Pro ring is significantly larger than the mass of the flexible Ala $^+$NH$_3$ moiety, it can absorb more thermal energy, which corresponds to its higher phase transition temperature.

Thus a simple change in residue order of the dipeptide results in dramatic changes in thermal stability and properties. Albeit a simplistic model, our results provide a molecular rationale for how thermophilic proteins can become more flexible at the relatively higher temperatures at which they function, and for the stabilizing effect of Pro residues at the N-terminal of an α-helix.

Ala-Pro and Pro-Ala VTR spectra readily exhibited the characteristics of longer range molecular order, even though only dipeptides. The frequency of the amide bond in Ala-Pro (1651 cm$^{-1}$) is consistent with an α-helical shape in larger peptides, while the amide in Pro-Ala (1674 cm$^{-1}$) is consistent with the β-sheet in larger peptides. These same wavenumbers are typically used to assign corresponding structural features to larger peptides, however Raman optical activity has determine that Ala dipeptide has secondary structure in aqueous solution. The chemical structure of eleven backbone atoms equals one loop of an α-helix and thus a dipeptide in the proper conformation equals slightly more than half an α-helix. Further VTR investigation of peptides and small proteins (solid state and in solution) is a logical next step towards a greater understanding of protein thermal transformation dynamics.

In operation, the variable temperature thermodynamic Raman spectroscopy method and apparatus described herein is a system for material analysis. In accordance with the system, a target material is subjected to a variable temperature thermodynamic protocol and analyzed using a rapid Raman spectroscopy system. Specifically, the dynamic response of the molecular structure to the thermal stress is not absorbed equally site to site with the absorption selectivity based upon molecular flexibility. The more flexible sites absorb thermal energy faster than the more rigid sites. During phase transitions, the sites at temperature at which are flexibility changes are highly specific and characteristic markers of identity and thermodynamic changes. The VTR measurement is unique because the temperature gradient enables distinguishing of vibrational modes that are due to kinetic processes from those that are due to steady-state processes; VTR identifies the precise temperature and/or temperature range over which molecular changes occur, and, concomitantly, the specific molecular sites most directly involved in these changes. The invention enables differentiation of more/most flexible sites (most temperature dependent) from more/most rigid sites (most temperature independent).

For the foregoing reasons, it is clear that the method and apparatus described herein provides an innovative method of analyzing target materials to more quickly and reliably determine the sub-molecular structure flexibility in a thermal stress/temperature gradient. The current system may be modified in multiple ways and applied in various technological applications. The disclosed method and apparatus may be modified and customized as required by a specific operation or application, and the individual components may be modified and defined, as required, to achieve the desired result.

Although the materials of construction are not generally described, they may include a variety of compositions consistent with the function described herein. Such variations are not to be regarded as a departure from the spirit and scope of this disclosure, and all such modifications as would be obvious to one skilled in the art are intended to be included within the scope of the following claims.

This information can be utilized to understand critical temperatures for manipulating complex molecules to engineer/synthesize new materials in many fields of application, such as biomedicine, biochemistry, and material science. The device and method will allow the understanding and manipulation of biopolymer folding, including protein folding.

What is claimed is:

1. A sample analysis system, the system comprising:
  a planar substrate;
  multiple elongated prongs extending perpendicular to the substrate and vertically supporting the substrate;
  a sample holder disposed in a center of the substrate, the substrate being configured to hold a target sample;
  thermocouples positioned on an opposite side of the substrate from the prongs, the thermocouples receiving and communicating temperature data;
  a Raman probe directed to the target sample, the Raman probe acquiring spectral data that is synced to the (corresponding) thermocouple data;
  a computer control system in communication with the thermocouples and the Raman probe;
  whereby as the sample holder increases in temperature, the Raman probe acquires Raman spectral data for the target sample, the data being synced with the corresponding thermocouple temperature data so that the spectral data is recorded with the corresponding temperature data.

2. The system of claim 1 wherein the substrate is circular and is comprised of copper.

3. The system of claim 1 wherein the sample holder comprises a cup attached to the substrate.

4. The system of claim 3 wherein the cup extends below the substrate.

5. The system of claim 4 wherein the substrate has an aperture in the center of the substrate.

6. The system of claim 5 wherein the system is configured so that the Raman probe directs a laser through the aperture to the target sample in the cup.

7. The system of claim 1 wherein the system is configured so that the elongated prongs are disposed on a heating device, the heating device heating the target sample by communicating heat through the prongs to the target sample in the sample holder, the Raman Probe acquiring spectral data as the target sample is heated.

8. The system of claim 7 wherein the Raman probe specifically acquires data as the target sample is heated through phase changes.

9. The system of claim 3 wherein the target sample in the cup is cooled below ambient temperature, the Raman probe acquiring spectral data for the target sample as the target sample warms to ambient temperature.

10. A method of acquiring Raman spectral data, the method comprising the steps of:
(a) providing the system described in claim 1;
(b) acquiring Raman spectral data as the target sample is heated or cooled through the solid/liquid and/or liquid/gas phase changes.

11. A method of acquiring Raman spectral data for a target sample comprising the steps of:
(a) providing a sample holder substrate;
(b) positioning at least one thermocouple on a top of the substrate, the at least one thermocouple acquiring thermocouple temperature data;
(c) placing a sample holder cup below an aperture in a center of the substrate;
(d) depositing the target sample in the sample holder cup;
(e) directing a Raman probe to the target sample so that the Raman probe acquires spectral data on the sample;
(f) connecting a computer control system that is in communication with the at least one thermocouple and the Raman probe; and,
(g) acquiring Raman spectral data for the target sample using the Raman probe;
(h) syncing the spectral data with the corresponding thermocouple temperature data as the sample holder increases in temperature, so that the spectral data is recorded with the corresponding temperature data.

12. The method of claim 11, wherein, in step (e) varying a temperature of the target sample so that the Raman probe gathers target sample data as the temperature of the target sample changes.

13. The method of claim 12 wherein, in step (e), Raman spectral measurements of the target sample are conducted when the target sample is between −200° C. and 400° C.

14. The method of claim 13 wherein, in step (e), the Raman spectral measurements of the target sample are conducted at intervals of less than 1° C.

15. A system for acquiring spectral data for a target sample, the system comprising providing a circular sample holder substrate with an aperture in a center of the substrate and cup attached to the center of the substrate so that a Raman probe directs a laser through the center of the substrate to a target sample in the cup;
wherein at least two thermocouples acquiring thermocouple temperature data are attached to a top of the substrate, a computer control system is in communication with the thermocouples and the Raman probe so that, as the sample holder increases in temperature, the Raman probe acquires Raman spectral data for the target sample, the data being synced with the corresponding thermocouple temperature data so that the spectral data is recorded with the corresponding temperature data.

16. The system of claim 15 wherein the substrate further comprises multiple prongs that are disposed on a heating device so that the target sample is heated through the prongs by the heating device, the Raman probe acquiring spectral data as the target sample is heated.

17. The system of claim 15 wherein the cup is removable and can be cooled to below ambient temperature so that the Raman probe acquires spectral data as the target sample warms to ambient temperature.

18. The system of claim 13 wherein the substrate is comprised of copper and the cup is aluminum.

19. The system of claim 15 wherein the system allows Raman spectral measurements of a sample material from −200° C. to 400° C. at less than 1° C. interval.

* * * * *